US008183225B2

(12) United States Patent
Cronstein et al.

(10) Patent No.: US 8,183,225 B2
(45) Date of Patent: May 22, 2012

(54) INHIBITION OF BONE RESORPTION USING MEDICAL IMPLANTS CONTAINING ADENOSINE RECEPTOR ANTAGONISTS

(75) Inventors: Bruce N. Cronstein, New York, NY (US); Zhong Sheng Peng, New York, NY (US)

(73) Assignee: New York University, New York, NY (US)

( * ) Notice: Subject to any disclaimer, the term of this patent is extended or adjusted under 35 U.S.C. 154(b) by 473 days.

(21) Appl. No.: 12/291,510

(22) Filed: Nov. 10, 2008

(65) Prior Publication Data

US 2009/0123510 A1    May 14, 2009

(51) Int. Cl.
*A01N 43/04* (2006.01)
*C07H 19/16* (2006.01)
*A61K 31/52* (2006.01)
*C07K 14/705* (2006.01)

(52) U.S. Cl. ............................... 514/46; 536/27.3
(58) Field of Classification Search .................. None
See application file for complete search history.

(56) References Cited

U.S. PATENT DOCUMENTS

| | | | | | |
|---|---|---|---|---|---|
| 5,891,863 | A | * | 4/1999 | Yates | 514/108 |
| 5,972,923 | A | * | 10/1999 | Simpkins et al. | 514/182 |
| 6,211,165 | B1 | * | 4/2001 | Liang et al. | 514/46 |
| 6,326,359 | B1 | * | 12/2001 | Monaghan et al. | 514/46 |
| 7,410,502 | B2 | * | 8/2008 | Ellingsen et al. | 623/23.53 |
| 7,470,687 | B2 | * | 12/2008 | Eggenweiler et al. | 514/241 |
| 2008/0051364 | A1 | * | 2/2008 | Fishman et al. | 514/45 |

FOREIGN PATENT DOCUMENTS

| | | |
|---|---|---|
| GB | 2 289 218 A | 11/1995 |
| WO | WO 2005/084653 | 9/2005 |
| WO | WO 2006/004884 | 5/2006 |
| WO | WO 2007/095161 | 8/2007 |
| WO | WO 2007/134271 | 11/2007 |

OTHER PUBLICATIONS

Mitchell et al., Am. J. Physiol 276 (Cell physiol. 45): C659-C666, 1999.*
Rath-Wolfson, et al, "IB MEGA, an A3 adenosine receptor agonist prevents bond resorption in rasts with adjuvant induced arthritis" US national Library of Medicine, Bethesda, MD, Jul. 2006.
Russell, et al: "Adenosine inhibition of lipopolysaccharide-induced interleukin-6 secretion by the osteoblastic cell line MG-63"; Calcified Tissue International (Oct. 2007) vol. 81, No. 4; pp. 316-326.
Moochhala, et al: "Expression of inducible nitric oxide synthase in mice . . . " European Journal of Pharmacology, (Dec. 1996) vol. 316, No. 2-3, pp. 287-296.
Lerner, et al: "Characterization of adenosine receptors in bone. Studies on the effect of adenosine analogues on cyclic AMP formation and bond resorption . . . " ACTA Physiologica Scandinavica, (Oct. 1987) vol. 131, No. 2, pp. 287-296.
Clinical and Experimental Rheumatology, Jul.-Aug. 2006 v. 24, n. 4 pp. 400-406.
Adenosine $A_{2B}$ Receptors as Therapeutic Targets, Drug Dev Res 45:198, 1998.
Feoktistov, et al., Trends Pharmacol Sci 19:148-153, 1998.
Ralevic, et al (1998) Pharmacological Reviews, Vo. 50:413-492.
Cronstein, et al., 1986 Journal of Clinical Investigation 78:760-770.
Cronstein, et al., 1983, Journal of Experimental Medicine 158:1160-1177.
Cronstein, 2005, Pharmacol. Rev 57:163-172.
Merrill, et al., Arth. Rheum. 40:1308-1315, 1997.

* cited by examiner

*Primary Examiner* — Lorraine Spector
(74) *Attorney, Agent, or Firm* — Klauber & Jackson LLC

(57) ABSTRACT

The invention provides methods and compositions for reducing or inhibiting bone resorption, osteoclast differentiation and stimulation and the loosening of medical prostheses by administering a compound or agent that modulates an adenosine receptor such as the adenosine $A_{2A}$ receptor, in particular, an agonist of an adenosine $A_{2A}$ receptor. The invention also extends to pharmaceutical compositions comprising such an agent that modulates an adenosine receptor such as an adenosine $A_{2A}$ agonist and to prosthetic devices containing such an agent that modulates an adenosine receptor such as an $A_{2A}$ agonist on one or more surfaces or within the prosthetic device such as, for example, suspended in the cement forming the prosthetic device.

25 Claims, 7 Drawing Sheets

Figure 3: Alcian blue and TRAP staining on femurs from 6- to 7-week-old $A_{2A}$ KO mice and control littermates Figure 5: Electron Micrograph Of Osteoclasts In WT and $A_{2A}$ KO Mice

INHIBITION OF BONE RESORPTION USING MEDICAL IMPLANTS CONTAINING ADENOSINE RECEPTOR ANTAGONISTS

FIELD OF THE INVENTION

The present invention relates to methods and compositions for reducing or inhibiting bone resorption, osteoclast differentiation and stimulation and the loosening of medical prostheses.

BACKGROUND OF THE INVENTION

Adenosine is a nucleoside that occurs naturally in mammals, which acts as a ubiquitous biochemical messenger. The heart, for instance, produces and releases adenosine in order to modulate heart rate and coronary vasodilation. Likewise, adenosine is produced in the kidney to modulate essential physiological responses, including glomerular filtration rate (GFR), electrolyte reabsorption, and renin secretion.

Adenosine is known to bind to and activate seven-transmembrane spanning G-protein coupled receptors, thereby eliciting a variety of physiological responses. There are 4 known subtypes of adenosine receptors (i.e., $A_1$, $A_{2A}$, $A_{2B}$, and $A_3$), which mediate different, and sometimes opposing, effects. For example, activation of the adenosine $A_1$ receptor, elicits an increase in renal vascular resistance, which leads to a decrease in glomerular filtration rate (GFR), while activation of the adenosine $A_{2A}$ receptor elicits a decrease in renal vascular resistance. Conversely, blockade of the $A_1$ adenosine receptor decreases afferent arteriole pressure, leading to an increase in GFR and urine flow, and sodium excretion. Furthermore, $A_{2A}$ adenosine receptors modulate coronary vasodilation, whereas $A_{2B}$ receptors have been implicated in mast cell activation, asthma, vasodilation, regulation of cell growth, intestinal function, and modulation of neurosecretion (See, Adenosine $A_{2B}$ Receptors as Therapeutic Targets, Drug Dev Res 45:198; Feoktistov et al., *Trends Pharmacol Sci* 19:148-153 and Ralevic, V and Burnstock, G. (1998), Pharmacological Reviews, Vol. 50: 413-492), and $A_3$ adenosine receptors modulate cell proliferation processes. Two receptor subtypes ($A_1$ and $A_{2A}$) exhibit affinity for adenosine in the nanomolar range while two other known subtypes $A_{2B}$ and $A_3$ are low-affinity receptors, with affinity for adenosine in the low-micromolar range. $A_1$ and $A_3$ adenosine receptor activation can lead to an inhibition of adenylate cyclase activity, while $A_{2A}$ and $A_{2B}$ activation causes a stimulation of adenylate cyclase.

It has been shown that adenosine, acting at specific cell surface receptors, has the potential to suppress inflammation and that inflammation itself may increase extracellular adenosine levels (Cronstein, et al., 1986, *Journal of Clinical Investigation* 78:760-770; Cronstein, et al., 1983, *Journal of Experimental Medicine* 158:1160-1177). Further, it has been demonstrated that adenosine mediates the anti-inflammatory effects of low-dose methotrexate therapy for Rheumatoid Arthritis (Reviewed in Cronstein, 2005, *Pharmacol Rev* 57:163-172). Exploration of the therapeutic and toxic properties of methotrexate in the treatment of RA has led to a number of other potentially important pre-clinical therapeutic developments. Methotrexate increases giant cell formation from peripheral blood monocytes and that this effect is mediated by adenosine acting at $A_1$ receptors (Merrill, et al., *Arth. Rheum.* 40:1308-1315). In addition, $A_{2A}$ receptor antagonists promote giant cell formation by diminishing the effect of endogenous adenosine although the $A_1$ receptor-mediated promotion of giant cell formation appears to dominate.

$A_1$ receptor antagonists completely block, in a dose-dependent fashion, osteoclast formation. Similarly, the $A_1$ receptor antagonists block osteoclast function (resorption of dentin). Six-month old $A_1$ KO mice demonstrate increased bone density. Their bones demonstrate diminished resorption, and some evidence indicates that the osteoclasts in the $A_1$ knock-out mice do not resorb bone. A murine model of post-menopausal osteoporosis, ovariectomy-induced bone loss, reveals that treatment of mice with an adenosine $A_1$ receptor antagonist completely prevents ovariectomy-induced bone loss. Adenosine $A_1$ receptors may be useful in treating and preventing osteoporosis.

Replacement of osteoarthritic or damaged hips and knees is among the most common surgical procedures performed in the United States and other developed countries. Excellent results are achieved in more than 95% of patients. Prosthodontic prostheses are also increasingly successful as well. However, aside from infectionm the most pressing difficulty in maintaining mobility is the development of bone resorption and loosening of the prosthesis leading to early reimplantation. There are two components to the bone resorption including an inflammatory reaction to debris from the prosthesis (ultra high molecular weight polyethylene debris). However, inflammation alone is not sufficient to induce bone resorption. Differentiation and stimulation of osteoclasts is required for the destruction of peri-prosthetic bone and bone loosening.

All publications, patent applications, patents and other reference material mentioned are incorporated by reference in their entirety. In addition, the materials, methods and examples are only illustrative and are not intended to be limiting. The citation of references herein shall not be construed as an admission that such is prior art to the present invention.

SUMMARY OF THE INVENTION

The invention relates to the application and use of modulators of an adenosine receptor, including agonists of an adenosine receptor, to inhibit bone resorption, inhibit differentiation and stimulation of osteoclasts, and to reduce loosening of medical prostheses.

In a first aspect, the invention provides a method for inhibiting bone resorption comprising administering to a subject a therapeutically effective amount of an adenosine receptor agonist, or an analog, derivative or combination thereof.

In a second aspect, the invention provides a method for inhibiting differentiation and stimulation of osteoclasts comprising administering to the subject a therapeutically effective amount of an adenosine receptor agonist, or an analog, derivative or combination thereof.

In a third aspect, the invention provides a method of inhibiting or reducing loosening of a medical prosthesis comprising administering to a subject an amount of an adenosine receptor agonist effective to inhibit or reduce bone resorption, or an analog, derivative or combination thereof.

For each of these three aspects, in one particular embodiment, the adenosine receptor of the present invention is selected from the group consisting of $A_1$, $A_{2A}$, $A_{2B}$ and $A_3$. In a more particular embodiment, the adenosine receptor is an $A_{2A}$ receptor, and the agonist is an adenosine receptor $A_{2A}$ agonist. In yet another embodiment, the adenosine receptor agonist inhibits more than one adenosine receptor.

In another particular embodiment, the adenosine receptor agonist is a selective adenosine receptor agonist. In still other particular embodiments, the adenosine receptor agonist is a non-selective adenosine receptor agonist.

In a more particular embodiment, the agent that agonizes an adenosine receptor is an adenosine $A_{2A}$ receptor agonist. The adenosine receptor agonist may be, for instance, a small organic molecule, a protein or peptide, a nucleic acid or an antibody.

In yet another more particular embodiment, the adenosine receptor agonist is capable of substantially stimulating the endogenous activity of the adenosine receptor substantially the same as though the adenosine receptor had encountered its natural, endogenous ligand.

In yet another particular embodiment, the adenosine receptor agonist, in many embodiments an adenosine $A_{2A}$ receptor agonist is administered via an implanted device.

In one particular embodiment, an effective amount of an adenosine receptor agonist may be used in combination with one or more drugs useful in inhibiting bone resorption or inhibiting differentiation or stimulation of osteoclasts or a combination of any of these agents.

Adenosine $A_{2A}$ receptor agonists are well known in the art. Many are disclosed in, for instance, U.S. Pat. Nos. 7,226,913 and 6,326,359 and in United States Patent Publication Nos. 20070225247, 20060100169, 20060034941, 20050261236, 20050182018, 20050171050, 20050020915 and 20040064039, the disclosures of which are herein incorporated by reference in their entireties. In another more particular embodiment, the drug is selected from the group consisting of CGS 21680, MRE-0094, IB-MECA and R-PIA, binodenoson, ATL146, for instance.

The adenosine receptor agonist may be administered alone or in combination with one or more other compounds or agents for inhibiting bone resorption, osteoclast differentiation and stimulation and prosthesis loosening. Such other compounds may be, for instance, anti-inflammatory compounds, bisphosphonates or growth factors. The adenosine receptor agonist may be administered with a second adenosine receptor agonist or with a less selective adenosine receptor agonist. (i.e. one that binds other adenosine receptors in addition to $A_{2A}$, for example $A_{2B}$, $A_1$ or $A_3$).

In one embodiment, the adenosine receptor agonist may be selective for the receptor, or it may be a non-selective adenosine receptor agonist, which may stimulate or mimic natural ligands of one or more of the following receptors: $A_1$, $A_{2A}$, $A_{2B}$ or $A_3$. In a preferred embodiment, the adenosine receptor agonist is an adenosine $A_{2A}$ receptor agonist.

A fourth aspect of the invention provides a cement, absorbable matrix or other substance containing an adenosine receptor modulator, in particular, an adenosine receptor agonist. In many instances, the cement, absorbable matrix or other substance containing an adenosine receptor modulator is present in a prosthetic device. The prosthetic device is useful for inhibiting osteoclast differentiation and stimulation, bone resorption, and prosthesis loosening. The adenosine receptor modulator such as an adenosine $A_{2A}$ receptor agonist may be present in a composition applied to one or more surfaces of the prosthetic device or the adenosine receptor modulating agent such as an adenosine $A_{2A}$ receptor agonist may be present within the cement or matrix. In some embodiments, the adenosine receptor modulating agent such as an adenosine $A_{2A}$ receptor agonist, may be present within the very matrix of the prosthetic device such as for instance within the cement, e.g. methylmethacrylate cement that forms the prosthetic device.

In a fifth aspect, the present invention provides a pharmaceutical composition comprising the adenosine receptor agonist alone or in combination with one or more compounds or agents effective for inhibiting bone resorption, osteoclast differentiation and stimulation and the loosening of medical prostheses. The adenosine receptor agonist and the one or more compounds or agents may be formulated and administered alone or together. The pharmaceutical composition(s) comprising the adenosine receptor agonist and the one or more compounds or agents may be administered concurrently or sequentially. In another particular embodiment, the one or more compounds or agents effective for inhibiting bone resorption, osteoclast differentiation and stimulation and the loosening of medical prostheses are selected from the group consisting of those effective for stimulating bone density and those effective for inhibiting or reducing inflammation. The pharmaceutical compositions may be delivered orally or parenterally. They may be delivered via the intravenous route, the intramuscular route, or the subcutaneous route. They may be delivered as an immediate release formulation or as a slow or sustained release formulation. In some particular embodiments, the compositions are delivered on the surface of a prosthetic device or are delivered in the very matrix of a prosthetic device.

In another more particular embodiment, the pharmaceutical composition comprising the adenosine receptor agonist may also contain one or more drugs selected from the group consisting of anti-inflammatory agents, growth factors, bone morphogenetic protein, soluble RANK.

Other objects and advantages will become apparent to those skilled in the art from a review of the following description which proceeds with reference to the following illustrative drawings.

BRIEF DESCRIPTION OF THE FIGURES

FIG. 1A provides measured mRNA levels of all four adenosine receptors obtained from osteoclasts derived from bone marrow osteoclast precursors, splenocyte osteoclast precursors or the murine cell line RAW264.7 which differentiates into osteoclast like cells thereby demonstrating expression of adenosine receptors in each cell line. FIG. 1B provides Western Blot analysis of bone marrow-derived osteoclast lysates demonstrating the presence of all four adenosine receptors.

DETAILED DESCRIPTION OF THE INVENTION

Figure 1:
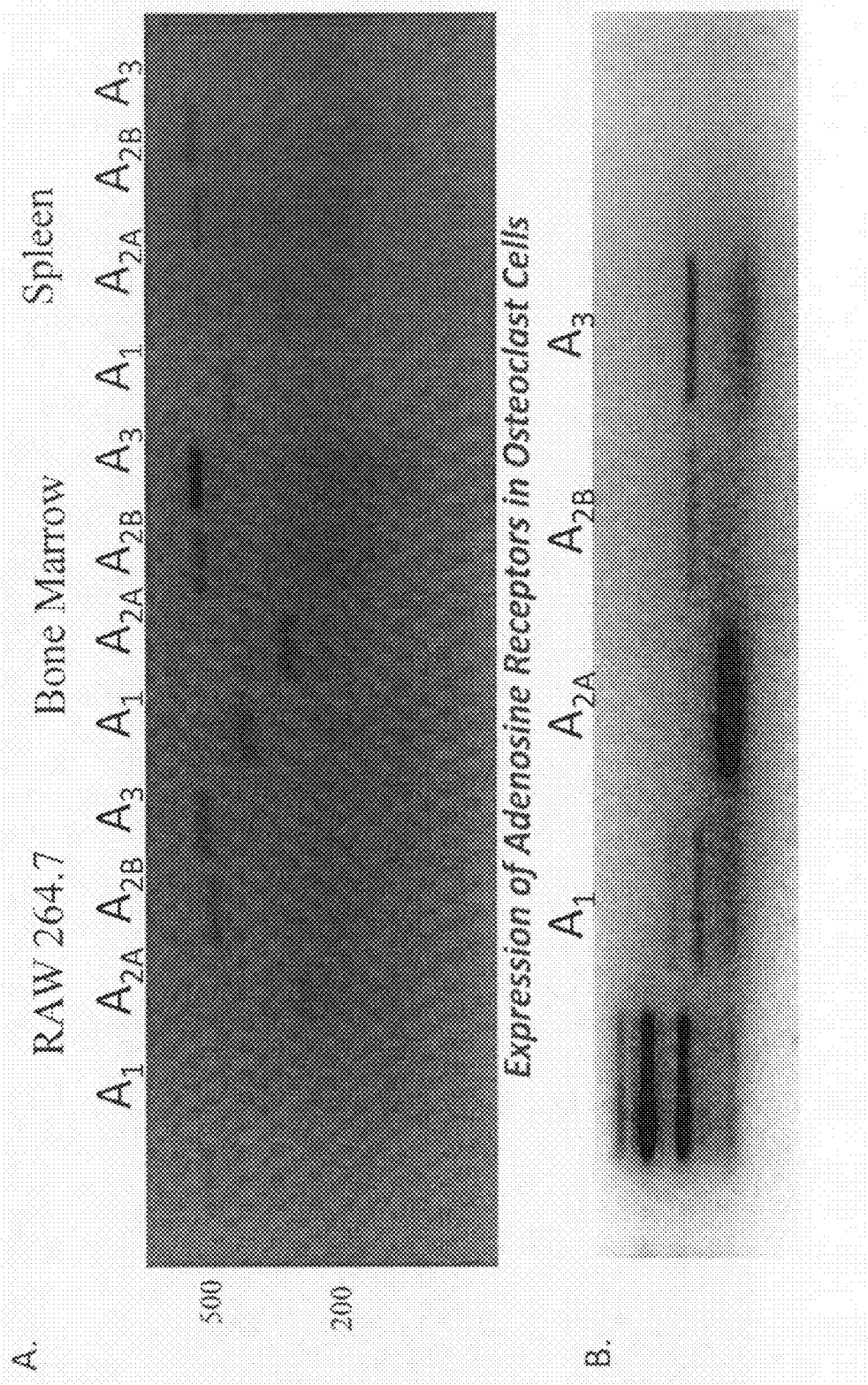
FIG. 1.

Before the present methods and treatment methodology are described, it is to be understood that this invention is not limited to particular methods and experimental conditions described, as such methods and conditions may vary. It is also to be understood that the terminology used herein is for purposes of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth in their entirety.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference I their entireties.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

DEFINITIONS

The terms used herein have the meanings recognized and known to those of skill in the art, however, for convenience and completeness, particular terms and their meanings are set forth below.

"Agent" refers to all materials that may be used to prepare pharmaceutical and diagnostic compositions, or that may be compounds such as small synthetic or naturally derived organic compounds, nucleic acids, polypeptides, antibodies, fragments, isoforms, variants, or other materials that may be used independently for such purposes, all in accordance with the present invention.

By "agonist" is meant a substance that binds to a specific receptor and triggers a response in a cell. It mimics the action of an endogenous ligand (such as hormone or neurotransmitter) that binds to the same receptor. A "full agonist" binds (has affinity for) and activates a receptor, displaying full efficacy at that receptor. One example of a drug that acts as a full agonist is isoproterenol which mimics the action of acetylcholine at β adrenoreceptors. A "partial agonist" (such as buspirone, aripiprazole, buprenorphine, or norclozapine) also binds and activates a given receptor, but has only partial efficacy at the receptor relative to a full agonist. A "partial agonist" may also be considered a ligand that displays both agonistic and antagonistic effects—when both a full agonist and partial agonist are present, the partial agonist actually acts as a competitive antagonist, competing with the full agonist for receptor occupancy and producing a net decrease in the receptor activation observed with the full agonist alone. A "co-agonist" works with other co-agonists to produce the desired effect together. An antagonist blocks a receptor from activation by agonists. Receptors can be activated or inactivated either by endogenous (such as hormones and neurotransmitters) or exogenous (such as drugs) agonists and antagonists, resulting in stimulating or inhibiting a biological response. A ligand can concurrently behave as agonist and antagonist at the same receptor, depending on effector pathways.

The potency of an agonist is usually defined by its $EC_{50}$ value. This can be calculated for a given agonist by determining the concentration of agonist needed to elicit half of the maximum biological response of the agonist. Elucidating an $EC_{50}$ value is useful for comparing the potency of drugs with similar efficacies producing physiologically similar effects. The lower the $EC_{50}$, the greater the potency of the agonist and the lower the concentration of drug that is required to elicit a maximum biological response.

"Antagonist" refers to an agent that down-regulates (e.g., suppresses or inhibits) at least one bioactivity of a protein. An "antagonist" or an agent that "antagonizes" may be a compound which inhibits or decreases the interaction between a protein and another molecule, e.g., a target peptide or enzyme substrate. An antagonist may also be a compound that downregulates expression of a gene or which reduces the amount of expressed protein present. Methods for assessing the ability of an agent to "antagonize" or "inhibit" an adenosine receptor are known to those skilled in the art.

"Analog" as used herein, refers to a chemical compound, a nucleotide, a protein, or a polypeptide that possesses similar or identical activity or function(s) as the chemical compounds, nucleotides, proteins or polypeptides having the desired activity and therapeutic effect of the present invention (e.g. to treat or prevent bone disease, or to modulate osteoclast differentiation), but need not necessarily comprise a compound that is similar or identical to those compounds of the preferred embodiment, or possess a structure that is similar or identical to the agents of the present invention.

"Derivative" refers to the chemical modification of molecules, either synthetic organic molecules or proteins, nucleic acids, or any class of small molecules such as fatty acids, or other small molecules that are prepared either synthetically or isolated from a natural source, such as a plant, that retain at least one function of the active parent molecule, but may be structurally different. Chemical modifications may include, for example, replacement of hydrogen by an alkyl, acyl, or amino group. It may also refer to chemically similar compounds which have been chemically altered to increase bioavailability, absorption, or to decrease toxicity. A derivative polypeptide is one modified by glycosylation, pegylation, or any similar process that retains at least one biological or immunological function of the polypeptide from which it was derived.

By "medical prosthetic device" or "prosthesis" is meant an artificial component, device or extension that replaces a portion or all of a body part whether the body part is entirely or partially missing. The term includes artificial limbs, breast prosthesis such as those implanted post-mastectomy, cochlear implants, corrective lenses, craniofacial prosthesis, dental/maxillofacial prosthetics such as those implanted to correct a cleft palate, dentures, dental restoration, facial prosthetics, hair prosthesis, neuroprosthetics, ocular prosthetics, ostomies such as colostomy, ileostomy and urostomy, penile prosthetics, replacement joints such as hips, knees and shoulders, simato prosthetics, prosthetic testis and transtibial prosthesis.

A "small molecule" refers to a molecule that has a molecular weight of less than 3 kilodaltons (kDa), preferably less than about 1.5 kilodaltons, more preferably less than about 1 kilodalton. Small molecules may be nucleic acids, peptides, polypeptides, peptidomimetics, carbohydrates, lipids or other organic (carbon-containing) or inorganic molecules. As those skilled in the art will appreciate, based on the present description, extensive libraries of chemical and/or biological mixtures, often fungal, bacterial, or algal extracts, may be screened with any of the assays of the invention to identify compounds that modulate a bioactivity. A "small organic molecule" is normally an organic compound (or organic compound complexed with an inorganic compound (e.g., metal)) that has a molecular weight of less than 3 kilodaltons, and preferably less than 1.5 kilodaltons, and more preferably less than about 1 kDa.

"Diagnosis" or "screening" refers to diagnosis, prognosis, monitoring, characterizing, selecting patients, including participants in clinical trials, and identifying patients at risk for or having a particular disorder or clinical event or those most likely to respond to a particular therapeutic treatment, or for assessing or monitoring a patient's response to a particular therapeutic treatment.

The concept of "combination therapy" is well exploited in current medical practice. Treatment of a pathology by combining two or more agents that target the same pathogen or biochemical pathway sometimes results in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect can be synergistic (the efficacy of the combination is greater than the sum of the effects of each drug given alone). As used herein, the term "combination therapy" means the two compounds can be delivered in a simultaneous manner, e.g. concurrently, or one of the compounds may be administered first, followed by the second agent, e.g sequentially. The desired result can be either a subjective relief of one or more symptoms or an objectively identifiable improvement in the recipient of the dosage.

"Differentiate" or "differentiation" as used herein, generally refers to the process by which precursor or progenitor cells differentiate into specific cell types. In the matter of the present invention, the term refers to the process by which pre-osteoclasts become osteoclasts. Differentiated cells can be identified by their patterns of gene expression and cell surface protein expression. As used herein, the term "differentiate" refers to having a different character or function from the original type of tissues or cells. Thus, "differentiation" is the process or act of differentiating. The term "Osteoclast Differentiation" refers to the process whereby osteoclast precursors in the bone marrow become functional osteoclasts.

"Modulation" or "modulates" or "modulating" refers to up regulation (i.e., activation or stimulation), down regulation (i.e., inhibition or suppression) of a response, or the two in combination or apart. As used herein, an adenosine receptor "modulator" or "modulating" compound or agent is a compound or agent that modulates at least one biological marker or biological activity characteristic of osteoclasts and bone formation. The term "modulating" as related to osteoclast differentiation, refers to the ability of a compound or agent to exert an effect on precursors to osteoclasts, or to alter the expression of at least one gene related to osteoclastogenesis. For example, expression of the following genes is modulated during osteoclastogenesis: DC-Stamp, tartrate resistant alkaline phosphatase (TRAP), cathepsin K, calcitonin receptor, and integrin.

As used herein, the term "candidate compound" or "test compound" or "agent" or "test agent" refers to any compound or molecule that is to be tested. As used herein, the terms, which are used interchangeably, refer to biological or chemical compounds such as simple or complex organic or inorganic molecules, peptides, proteins, oligonucleotides, polynucleotides, carbohydrates, or lipoproteins. A vast array of compounds can be synthesized, for example oligomers, such as oligopeptides and oligonucleotides, and synthetic organic compounds based on various core structures, and these are also included in the terms noted above. In addition, various natural sources can provide compounds for screening, such as plant or animal extracts, and the like. Compounds can be tested singly or in combination with one another. Agents or candidate compounds can be randomly selected or rationally selected or designed. As used herein, an agent or candidate compound is said to be "randomly selected" when the agent is chosen randomly without considering the specific interaction between the agent and the target compound or site. As used herein, an agent is said to be "rationally selected or designed", when the agent is chosen on a nonrandom basis which takes into account the specific interaction between the agent and the target site and/or the conformation in connection with the agent's action.

"Treatment" or "treating" refers to therapy, prevention and prophylaxis and particularly refers to administering medicine or performing medical procedures on a patient, for either prophylaxis (prevention) or to cure or reduce the extent of or likelihood of occurrence of the infirmity or malady or condition or event. In the present invention, the treatments using the agents described may be provided to slow or halt bone loss, or to increase the amount or quality of bone density. Most preferably, the treating is for the purpose of reducing or diminishing bone resorption and resultant prosthetic device loosening. Treating as used herein also means administering the compounds for increasing bone density or for modulating osteoclastogenesis in individuals. Furthermore, in treating a subject, the compounds of the invention may be administered to a subject already suffering from loss of bone mass or other bone disease as provided herein or to prevent or inhibit the occurrence of such condition.

"Subject" or "patient" refers to a mammal, preferably a human, in need of treatment for a condition, disorder or disease.

"Osteoclastogenesis" refers to osteoclast generation, which is a multi-step process that can be reproduced in vitro.

Earlier in vitro osteoclastogenesis systems used mixtures of stromal or osteoblastic cells together with osteoclast precursors from bone marrow (Suda, et al., (1997) *Methods Enzymol.* 282, 223-235; David et al., (1998) *J. Bone Miner. Res.* 13, 1730-1738). These systems utilized 1α, 25-dihydroxyvitamin $D_3$ to stimulate stromal/osteoblastic cells to produce factors that support osteoclast formation More recent models utilize bone marrow cells cultured with soluble forms of the cytokines M-CSF (macrophage-colony stimulating factor) and a soluble form of RANKL (receptor activator of nuclear factor KB ligand) (Lacey, et al., (1998) *Cell* 93, 165-176; Shevde et al., (2000) *Proc. Natl. Acad. Sci. U.S.A.* 97, 7829-7834). These two cytokines are now recognized as the major factors from stromal cells that support osteoclastogenesis (Takahashi, et al., (1999) *Biochem. Biophys. Res. Commun.* 256, 449-455). Thus, their addition to the culture medium overcomes the need for stromal cells.

"Osteoclast precursor" refers to a cell or cell structure, such as a pre-osteoclast, which is any cellular entity on the pathway of differentiation between a macrophage and a differentiated and functional osteoclast. The term osteoclast includes any osteoclast-like cell or cell structure which has differentiated fully or partially from a macrophage, and which has osteoclast character, including but not limited to positive staining for tartrate-resistant acid phosphatase (TRAP), but which is not a fully differentiated or functional osteoclast, including particularly aberrantly differentiated or non functional osteoclasts or pre-osteoclasts.

"Osteoclast culture" refers to any in vitro or ex vivo culture or system for the growth, differentiation and/or functional assessment of osteoclasts or osteoclast precursors, whether in the absence or presence of other cells or cell types, for instance, but not limited to, osteoblasts, macrophages, hematopoietic or stromal cells.

"Osteoclast function", as used herein, refers to bone resorption and the processes required for bone resorption.

An "amount sufficient to inhibit osteoclast differentiation, formation or function" refers to the amount of the adenosine receptor agonist sufficient to block either the differentiation, the formation or the function of osteoclasts, more particularly, an amount ranging from about 0.1 nM to about 10 μM, or more preferentially from about 0.1 nM to about 5 μM, and most preferentially from about 0.1 nM to about 1 μM in vitro. In vivo amounts of an adenosine receptor agonist such as an adenosine $A_{2A}$ receptor agonist sufficient to block either the differentiation, the formation or the function of osteoclasts may range from about 0.1 mg/Kg of body weight per day to about 200 mg/Kg of body weight per day in vivo, or more preferentially from about 1 mg/Kg to about 100 mg/Kg, and most preferentially from about 25 mg/Kg to about 50 mg/Kg of body weight per day in vivo. It is understood that the dose, when administered in vivo, may vary depending on the clinical circumstances, such as route of administration, age, weight and clinical status of the subject in which inhibition of osteoclast differentiation, formation or function is desired.

In a specific embodiment, the term "about" means within 20%, preferably within 10%, and more preferably within 5%.

An "effective amount" or a "therapeutically effective amount" is an amount sufficient to decrease or prevent the symptoms associated with the conditions disclosed herein, including bone loss or in a decrease in bone mass or density, such as that which occurs with medical prosthetic devices or other related conditions contemplated for therapy with the compositions of the present invention. For example, an "effective amount" for therapeutic uses is the amount of the composition comprising an active compound herein required to provide reversal or inhibition of bone loss or delay the onset of prosthetic device loosening, increase and/or accelerate bone growth into prosthetic devices, etc. Such effective amounts may be determined using routine optimization techniques and are dependent on the particular condition to be treated, the condition of the subject, the route of administration, the formulation, and the judgment of the practitioner and other factors evident to those skilled in the art. The dosage required for the compounds of the invention is that which induces a statistically significant difference in bone mass or inhibition of bone loss between treatment and control groups. This difference in bone mass or bone loss may be seen, for example, as at least 1-2%, or any clinically significant increase in bone mass or reduction in bone loss in the treatment group. Other measurements of clinically significant increases in healing may include, for example, an assay for the N-terminal propeptide of Type I collagen, tests for breaking strength and tension, breaking strength and torsion, 4-point bending, increased connectivity in bone biopsies and other biomechanical tests well known to those skilled in the art. General guidance for treatment regimens may be obtained from experiments carried out in vitro or in animal models of the disease of interest. The "effective amount" or "therapeutically effective amount" may range from about 1 mg/Kg to about 200 mg/Kg in vivo, or more preferentially from about 10 mg/Kg to about 100 mg/Kg, and most preferentially from about 25 mg/Kg to about 50 mg/Kg in vivo.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Binding compounds can also be characterized by their effect on the activity of the target molecule. Thus, a "low activity" compound has an inhibitory concentration ($IC_{50}$) (for inhibitors or antagonists) or effective concentration ($EC_{50}$) (applicable to agonists) of greater than 1 μM under standard conditions. By "very low activity" is meant an $IC_{50}$ or $EC_{50}$ of above 100 μM under standard conditions. By "extremely low activity" is meant an $IC_{50}$ or $EC_{50}$ of above 1 mM under standard conditions. By "moderate activity" is meant an $IC_{50}$ or $EC_{50}$ of 200 nM to 1 μM under standard conditions. By "moderately high activity" is meant an $IC_{50}$ or $EC_{50}$ of 1 μM to 200 nM. By "high activity" is meant an $IC_{50}$ or $EC_{50}$ of below 1 nM under standard conditions. The $IC_{50}$ (or $EC_{50}$) is defined as the concentration of compound at which 50% of the activity of the target molecule (e.g., enzyme or other protein) activity being measured is lost (or gained) relative to activity when no compound is present. Activity can be measured using methods known to those of ordinary skill in the art, e.g., by measuring any detectable product or signal produced by occurrence of an enzymatic reaction, or other activity by a protein being measured.

An individual "at risk" may or may not have detectable disease, and may or may not have displayed detectable disease prior to the treatment methods described herein. "At risk" denotes that an individual who is determined to be more likely to develop a symptom based on conventional risk assessment methods or has one or more risk factors that correlate with development of a bone disease or low bone mass or density or enhanced susceptibility to bone resorption. An individual having one or more of these risk factors has a higher probability of developing bone resorption than an individual without these risk factors.

"Prophylactic" or "therapeutic" treatment refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

General Description

The invention relates to the unexpected finding that stimulating an adenosine receptor such as an adenosine $A_{2A}$ receptor with agents that are agonists of the receptor leads to or results in inhibition of osteoclast differentiation, formation, or function, leads to less bone resorption, and subsequently leads to less loosening of surgically implanted medical prostheses. As such, these agonists may be used to treat a subject having a condition characterized by bone loss that may lead to subsequent loosening of a medical prosthesis. These agonists may be especially well suited for treating bone loss associated with prosthetic implantation, other forms of osteopenia, and in other conditions where facilitation of bone repair or replacement is desired such as bone fractures, bone defects, plastic surgery, dental and other implantations. Likewise, these agonists such as adenosine $A_{2A}$ receptor agonists may be used to increase bone mass or may ameliorate loss of bone mass in any of these conditions. It was determined that adenosine $A_{2A}$ receptor occupancy blocks osteoclast formation by murine splenocytes incubated with macrophage colony stimulating factor (M-CSF) and receptor activator of NFkB ligand (RANKL) in vitro. Animals lacking adenosine $A_{2A}$ receptors suffer from diminished bone mass in vivo. These results suggest that adenosine $A_{2A}$ receptor agonists may be useful in the treatment of osteoporosis, prosthetic joint loosening and other conditions in which osteoclasts play a pathogenic role (e.g. Paget's Disease).

Adenosine, a potent endogenous physiological mediator, regulates a wide variety of physiological processes via interaction with one or more of four G protein-coupled receptors ($A_1$, $A_{2A}$, $A_{2B}$, and $A_3$), expressed on many cell types, including neutrophils, macrophages, fibroblasts, and endothelial cells. Because adenosine $A_{2A}$ receptors inhibit the formation of giant cells from peripheral blood monocytes in vitro it was determined that adenosine, acting through one or another of these receptors, regulated the formation of osteoclasts.

Osteoclast formation is reduced by adenosine $A_{2A}$ receptor occupancy since pharmacologic blockade of these receptors completely inhibits the formation of osteoclasts in vitro.

In one embodiment, agents that interact with (e.g., bind to) and block, agonize or stimulate an adenosine receptor, in particular, $A_{2A}$ (e.g., a functionally active fragment), are identified in a cell-based assay system. In accordance with this embodiment, cells expressing an adenosine receptor, a fragment of an adenosine receptor, an adenosine receptor related polypeptide, or a binding fragment thereof, are contacted with a candidate compound or a control compound and the ability of the candidate compound to interact with the receptor or fragment thereof is determined. Alternatively, the ability of a candidate compound to compete for binding with a known ligand or compound known to bind the receptor is measured. If desired, this assay may be used to screen a plurality (e.g. a library) of candidate compounds. The cell, for example, can be of prokaryotic origin (e.g., E. coli) or eukaryotic origin (e.g., yeast, insect or mammalian). Further, the cells can express the receptor endogenously or be genetically engineered to express the receptor, a binding fragment or a receptor fusion protein. In some embodiments, the receptor or fragment thereof, or the candidate compound is labeled, for example with a radioactive label (such as $^{32}P$, $^{35}S$ or $^{125}I$) or a fluorescent label (such as fluorescein isothiocyanate, rhodamine, phycoerythrin, phycocyanin, allophycocyanin, o-phthaldehyde or fluorescamine) to enable detecting an interaction between the $A_{2A}$ receptor and a candidate compound. The ability of the candidate compound to interact directly or indirectly with a receptor or binding fragment thereof or a fusion protein or to modulate the activity of the receptor can be determined by methods known to those of skill in the art. For example, the interaction or modulation by a candidate compound can be determined by flow cytometry, a scintillation assay, immunoprecipitation or western blot analysis, based on the present description, or by a competitive radioreceptor assay.

Selecting the compounds that interact with or bind to an adenosine receptor or otherwise agonize or stimulate the receptor may be performed in multiple ways. The compounds may first be chosen based on their structural and functional characteristics, using one of a number of approaches known in the art. For instance, homology modeling can be used to screen small molecule libraries in order to determine which molecules would be candidates to interact with the receptor thereby selecting plausible targets. The compounds to be screened can include both natural and synthetic ligands. Furthermore, any desired compound may be examined for its ability to interact with or bind to the receptor.

Binding to or interaction with adenosine receptors may be determined by performing an assay such as, for example, a binding assay between a desired compound and an adenosine receptor. In one aspect, this is done by contacting said compound to an adenosine receptor and determining its dissociation rate. Numerous possibilities for performing binding assays are well known in the art. The indication of a compound's ability to bind to an adenosine receptor is determined, e.g., by a dissociation rate, and the correlation of binding activity and dissociation rates is well established in the art. For example, the assay may be performed by radiolabeling a reference compound, or other suitable radioactive marker, and incubating it with the cell bearing an adenosine receptor, in particular, $A_{2A}$. Test compounds are then added to these reactions in increasing concentrations. After optimal incubation, the reference compound and receptor complexes are separated, e.g., with chromatography columns, and evaluated for bound $^{125}I$-labeled peptide with a gamma (γ) counter. The amount of the test compound necessary to inhibit 50% of the reference compound's binding is determined. These values are then normalized to the concentration of unlabeled reference compound's binding (relative inhibitory concentration $(RIC)^{-1}$=concentration$_{test}$/concentration$_{reference}$). A small $RIC^{-1}$ value indicates strong relative binding, whereas a large $RIC^{-1}$ value indicates weak relative binding. See, for example, Latek et al., *Proc. Natl. Acad. Sci. USA*, Vol. 97, No. 21, pp. 11460-11465, 2000. An adenosine receptor agonist mimic may be computationally evaluated and designed by means of a series of steps in which chemical groups or fragments are screened and selected for their ability to associate with the individual binding pockets or interface surfaces of the protein (e.g. the $A_{2A}$ receptor). One skilled in the art may employ one of several methods to screen chemical groups or fragments for their ability to associate with the adenosine receptor. This process may begin by visual inspection of, for example, the protein/protein interfaces or the binding site on a computer screen based on the available crystal complex coordinates of the receptor, including a protein known to interact with selected fragments or chemical groups may then be positioned in a variety of orientations, or docked, at an individual surface of the receptor that participates in a protein/protein interface or in the binding pocket. Docking may be accomplished using software such as QUANTA and SYBYL, followed by energy minimization and molecular dynamics with standard molecular mechanics forcefields, such as CHARMM and AMBER (AMBER, version 4.0 (Kollman, University of California at San Francisco, copyright, 1994); QUANTA/CHARMM (Molecular Simulations, Inc., Burlington, Mass., copyright, 1994)). Specialized computer programs may also assist in the process of selecting fragments or chemical groups. These include: GRID (Goodford, 1985, *J. Med. Chem.* 28:849-857), available from Oxford University, Oxford, UK; MCSS (Miranker & Karplus, 1991, Proteins: Structure, Function and Genetics 11:29-34), available from Molecular Simulations, Burlington, Mass.; AUTODOCK (Goodsell & Olsen, 1990, Proteins: Structure, Function, and *Genetics* 8:195-202), available from Scripps Research Institute, La Jolla, Calif.; and DOCK (Kuntz et al., 1982, *J. Mol. Biol.* 161:269-288), available from University of California, San Francisco, Calif. Once suitable chemical groups or fragments that bind to an adenosine receptor have been selected, they can be assembled into a single compound or agonist. Assembly may proceed by visual inspection of the relationship of the fragments to each other in the three-dimensional image displayed on a computer screen in relation to the structure coordinates thereof. This would be followed by manual model building using software such as QUANTA or SYBYL. Useful programs to aid one of skill in the art in connecting the individual chemical groups or fragments include: CAVEAT (Bartlett et al., 1989, 'CAVEAT: A Program to Facilitate the Structure-Derived Design of Biologically Active Molecules'. In Molecular Recognition in Chemical and Biological Problems', Special Pub., Royal Chem. Soc. 78:182-196), available from the University of California, Berkeley, Calif.; 3D Database systems such as MACCS-3D (MDL Information Systems, San Leandro, Calif.). This area is reviewed in Martin, 1992, *J. Med. Chem.* 35:2145-2154); and HOOK (available from Molecular Simulations, Burlington, Mass.). Instead of proceeding to build an adenosine receptor agonist mimic, in a step-wise fashion one fragment or chemical group at a time, as described above, such compounds may be designed as a whole or 'de novo' using either an empty binding site or the surface of a protein that participates in protein/protein interactions or optionally including some portion(s) of a known activator(s). These methods include: LUDI (Bohm, 1992, *J. Comp. Aid. Molec. Design* 6:61-78), available from Molecular Simulations, Inc., San Diego, Calif.; LEGEND (Nishibata et al., 1991, *Tetrahedron* 47:8985), available from Molecular Simulations, Burlington, Mass.; and LeapFrog (available from Tripos, Inc., St. Louis, Mo.). Other molecular modeling techniques may also be employed in accordance with this invention. See, e.g., Cohen et al., 1990, *J. Med. Chem.* 33:883-894. See also, Navia & Murcko, 1992, *Current Opinions in Structural Biology* 2:202-210.

Once a compound has been designed by the above methods, the efficiency with which that compound may bind to or interact with the adenosine receptor protein may be tested and optimized by computational evaluation. Agonists may interact with the receptor in more than one conformation that is similar in overall binding energy. In those cases, the deformation energy of binding is taken to be the difference between the energy of the free compound and the average energy of the conformations observed when the inhibitor binds to the receptor protein.

A compound selected for binding to the adenosine receptor may be further computationally optimized so that in its bound state it would preferably lack repulsive electrostatic interaction with the target protein. Such non-complementary electrostatic interactions include repulsive charge-charge, dipole-dipole and charge-dipole interactions. Specifically, the sum of all electrostatic interactions between the compound and the receptor protein when the mimic is bound to it preferably make a neutral or favorable contribution to the enthalpy of binding. Specific computer software is available in the art to evaluate compound deformation energy and electrostatic interaction. Examples of programs designed for such uses include: Gaussian 92, revision C (Frisch, Gaussian, Inc., Pittsburgh, Pa. copyright 1992); AMBER, version 4.0 (Kollman, University of California at San Francisco, copyright 1994); QUANTA/CHARMM (Molecular Simulations, Inc., Burlington, Mass., copyright 1994); and Insight II/Discover (Biosym Technologies Inc., San Diego, Calif., copyright 1994). These programs may be implemented, for instance, using a computer workstation, as are well-known in the art. Other hardware systems and software packages will be known to those skilled in the art.

Once an adenosine receptor modulating compound, preferably an agonist, has been optimally designed, for example as described above, substitutions may then be made in some of its atoms or chemical groups in order to improve or modify its binding properties, or its pharmaceutical properties such as stability or toxicity. Generally, initial substitutions are conservative, i.e., the replacement group will have approximately the same size, shape, hydrophobicity and charge as the original group. Substitutions known in the art to alter conformation should be avoided. Such altered chemical compounds may then be analyzed for efficiency of binding to the receptor by the same computer methods described in detail above.

Candidate Compounds and Agents

Examples of agents, candidate compounds or test compounds include, but are not limited to, nucleic acids (e.g., DNA and RNA), carbohydrates, lipids, proteins, peptides, peptidomimetics, small molecules and other drugs. In one preferred aspect, agents can be obtained using any of the numerous suitable approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, *Anticancer Drug Des.* 12:145; U.S. Pat. No. 5,738,996 and U.S. Pat. No. 5,807,683).

Phage display libraries may be used to screen potential ligands or adenosine receptor modulators. Their usefulness lies in the ability to screen, for example, a library displaying a large number of different compounds. For use of phage display libraries in a screening process, see, for instance, Kay et al., *Methods,* 240-246, 2001. An exemplary scheme for using phage display libraries to identify compounds that bind or interact with an adenosine receptor may be described as follows: initially, an aliquot of the library is introduced into microtiter plate wells that have previously been coated with target protein, e.g. $A_{2A}$ receptor. After incubation (e.g., 2 hours), the nonbinding phage are washed away, and the bound phage are recovered by denaturing or destroying the target with exposure to harsh conditions such as, for instance pH 2, but leaving the phage intact. After transferring the phage to another tube, the conditions are neutralized, followed by infection of bacteria with the phage and production of more phage particles. The amplified phage are then rescreened to complete one cycle of affinity selection. After three or more rounds of screening, the phage are plated out such that there are individual plaques that can be further analyzed. For example, the conformation of binding activity of affinity-purified phage for the adenosine $A_{2A}$ receptor may be obtained by performing ELISAs. One skilled in the art can easily perform these experiments. In one aspect, an $A_{2A}$ receptor molecule used for any of the assays may be a recombinant $A_{2A}$ receptor protein, or an $A_{2A}$ fusion protein, an analog, derivative, or mimic thereof.

Examples of methods for the synthesis of molecular libraries can be found in the art, for example in: DeWitt et al., 1993, *Proc. Natl. Acad. Sci. USA* 90:6909; Erb et al., 1994, *Proc. Natl. Acad. Sci. USA* 91:11422; Zuckermann et al., 1994, *J. Med. Chem.* 37:2678; Cho et al., 1993, *Science* 261:1303; Carrell et al., 1994, Angew. *Chem. Int. Ed. Engl.* 33:2059; Carell et al., 1994, *Angew. Chem. Int. Ed. Engl.* 33:2061; and Gallop et al., 1994, *J. Med. Chem.* 37:1233.

Libraries of compounds may be presented, e.g., in solution (Houghten, 1992, *Bio/Techniques* 13:412-421), or on beads (Lam, 1991, *Nature* 354:82-84), chips (Fodor, 1993, *Nature* 364:555-556), bacteria (U.S. Pat. No. 5,223,409), spores (U.S. Pat. Nos. 5,571,698; 5,403,484; and 5,223,409), plasmids (Cull et al., 1992, *Proc. Natl. Acad. Sci. USA* 89:1865-1869) or phage (Scott and Smith, 1990, *Science* 249:386-390; Devlin, 1990, Science 249:404-406; Cwirla et al., 1990, *Proc. Natl. Acad. Sci. USA* 87:6378-6382; and Felici, 1991, *J. Mol. Biol.* 222:301-310).

The methods of screening compounds may also include the specific identification or characterization of such compounds, whose effect on bone resorption was determined by the methods described above. If the identity of the compound is known from the start of the experiment, no additional assays are needed to determine its identity. However, if the screening for compounds that modulate the adenosine $A_{2A}$ receptor is done with a library of compounds, it may be necessary to perform additional tests to positively identify a compound that satisfies all required conditions of the screening process. There are multiple ways to determine the identity of the compound. One process involves mass spectrometry, for which various methods are available and known to the skilled artisan (e.g. the neogenesis website). Neogenesis' ALIS (automated ligand identification system) spectral search engine and data analysis software allow for a highly specific identification of a ligand structure based on the exact mass of the ligand. One skilled in the art can also readily perform mass spectrometry experiments to determine the identity of the compound.

Antibodies, including polyclonal and monoclonal antibodies, particularly anti-$A_{2A}$ receptor antibodies and neutralizing antibodies may be useful as compounds to modulate osteoclast differentiation and/or function. These antibodies are available from such vendors as Upstate Biologicals, Santa Cruz, or they made be prepared using standard procedures for preparation of polyclonal or monoclonal antibodies known to those skilled in the art. Also, antibodies including both polyclonal and monoclonal antibodies, and drugs that modulate the activity of the adenosine receptor and/or its subunits may possess certain diagnostic applications and may for example, be utilized for the purpose of detecting and/or measuring conditions such as bone diseases, bone loss, or osteoclast differentiation and/or function. The adenosine receptor or its subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or act as agonists for the activities of the $A_{2A}$ receptor may be discovered or synthesized, and may be used in diagnostic and/or therapeutic protocols.

Therapeutic and Prophylactic Compositions and Their Use

Candidates for therapy with the agents identified by the methods described herein are patients either suffering from bone resorption or patients who have a medical prosthesis implanted or who contemplate receiving an implant medical prosthetic device.

The invention provides methods of treatment featuring administering to a subject an effective amount of an agent of the invention. The compound is preferably substantially purified (e.g., substantially free from substances that limit its effect or produce undesired side-effects). The subject is preferably an animal, including but not limited to animals such as monkeys, cows, pigs, horses, chickens, cats, dogs, etc., and is preferably a mammal, and most preferably human. In one specific embodiment, a non-human mammal is the subject. In another specific embodiment, a human mammal is the subject. Accordingly, the agents identified by the methods described herein may be formulated as pharmaceutical compositions to be used for prophylaxis or therapeutic use to treat these patients.

Various delivery systems are known and can be used to administer a compound of the invention, e.g., encapsulation in liposomes, microparticles, or microcapsules. Methods of introduction can be enteral or parenteral and include but are not limited to intradermal, intramuscular, intraperitoneal, intravenous, subcutaneous, intranasal, epidural, topical and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. In a specific embodiment, it may be desirable to administer the pharmaceutical compositions of the invention locally to the area in need of treatment.

Such compositions comprise a therapeutically effective amount of an agent, and a pharmaceutically acceptable carrier. In a particular embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In another embodiment, the compound can be delivered in a vesicle, in particular a liposome (Langer (1990) Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327)

In yet another embodiment, the compound can be delivered in a controlled or sustained release system. In one embodiment, a pump may be used (see Langer, supra; Sefton (1987) CRC Crit. Ref. Biomed. Eng. 14:201; Buchwald et al. (1980) Surgery 88:507; Saudek et al. (1989) N. Engl. J. Med. 321: 574). In another embodiment, polymeric materials can be used (See, Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger et al., (1983) Macromol. Sci. Rev. Macromol. Chem. 23:61; Levy et al. (1985) Science 228:190; During et al. (1989) Ann. Neurol. 25:351; Howard et al. (1989) J. Neurosurg. 71:105). In yet another embodiment, a controlled release system can be placed in proximity of the therapeutic target, i.e., the subject bone or prosthesis, thus requiring only a fraction of the systemic dose (see, e.g., Goodson, in Medical Applications of Controlled Release (1984) supra, vol. 2, pp. 115-138). Other suitable controlled release systems are discussed in the review by Langer (1990) Science 249:1527-1533.

The present invention further contemplates therapeutic compositions useful in practicing the therapeutic methods of this invention. A subject therapeutic composition includes, in admixture, a pharmaceutically acceptable excipient (carrier) and one or more of an adenosine receptor modulator, such as an adenosine $A_{2A}$ receptor agonist, as described herein as an active ingredient. In a preferred embodiment, the composition comprises one or more compounds or agents capable of mimicking or serving as an agonist for the adenosine $A_{2A}$ receptor.

Effects of the compounds or agents of the invention can first be tested for their ability to stimulate or mimic the adenosine receptor using standard techniques known in the art. More particularly, the selectivity of the compounds for the receptor can be assessed using radioligand binding assays whereby a test or candidate compound can be assayed for its ability to bind to a cell having or expressing the receptor (including any of the known adenosine receptors, $A_1$, $A_{2A}$, $A_{2B}$ or $A_3$). Cells can be transfected with the nucleic acid encoding the various adenosine receptors and competitive binding assays with radiolabeled ligands run to evaluate the specificity of the particular candidate compounds. The cDNAs for human $A_1$ (see GenBank accession number BC026340), $A_{2A}$ (see GenBank accession number $NM_{000675}$), $A_{2B}$ (see GenBank accession number $NM_{000676}$) or $A_3$ (see GenBank accession number AY136749 or L22607 or $NM_{000677}$) can be used to prepare the nucleic acid constructs for use in these methods.

The present compounds or agents that modulate the adenosine receptor, in particular, the agonists of the $A_{2A}$ receptor, themselves can be used as the sole active agents, or can be used in combination with one or more other active ingredients. In particular, combination therapy using the adenosine receptor agonists with one or more other agents is contemplated. These agents are known in the art, and can be selected from anti-inflammatory compounds, bisophosphonates, soluble RANK, and bone morphogenetic proteins, for instance.

When contemplating combination therapy with an adenosine receptor agonist and one or more of the above-noted agents, it is important to assess clinical safety by methods known to those skilled in the art. Appropriate dose titration may be necessary when certain groups of compounds are contemplated for use together.

The compounds or compositions of the invention may be combined for administration with or embedded in polymeric carrier(s), biodegradable or biomimetic matrices or in a scaffold. The carrier, matrix or scaffold may be of any material that will allow composition to be incorporated and expressed and will be compatible with the addition of cells or in the presence of cells. Preferably, the carrier matrix or scaffold is predominantly non-immunogenic and is biodegradable. Examples of biodegradable materials include, but are not limited to, polyglycolic acid (PGA), polylactic acid (PLA), hyaluronic acid, catgut suture material, gelatin, cellulose, nitrocellulose, collagen, albumin, fibrin, alginate, cotton, or other naturally-occurring biodegradable materials. It may be preferable to sterilize the matrix or scaffold material prior to administration or implantation, e.g., by treating it with ethylene oxide or by gamma irradiation or irradiation with an electron beam. In addition, a number of other materials may be used to form the scaffold or framework structure, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE, teflon), thermanox (TPX), polymers of hydroxy acids such as polylactic acid (PLA), polyglycolic acid (PGA), and polylactic acid-glycolic acid (PLGA), polyorthoesters, polyanhydrides, polyphosphazenes, and a variety of polyhydroxyalkanoates, and combinations thereof. Matrices suitable include a polymeric mesh or sponge and a polymeric hydrogel. In the preferred embodiment, the matrix is biodegradable over a time period of less than a year, more preferably less than six months, most preferably over two to ten weeks. The polymer composition, as well as method of manufacture, can be used to determine the rate of degradation. For example, mixing increasing amounts of polylactic acid with polyglycolic acid decreases the degradation time. Meshes of polyglycolic acid that can be used can be obtained commercially, for instance, from surgical supply companies (e.g., Ethicon, N.J.). A hydrogel is defined as a substance formed when an organic polymer (natural or synthetic) is cross-linked via covalent, ionic, or hydrogen bonds to create a three-dimensional open-lattice structure which entraps water molecules to form a gel. In general, these polymers are at least partially soluble in aqueous solutions, such as water, buffered salt solutions, or aqueous alcohol solutions, that have charged side groups, or a monovalent ionic salt thereof.

For use in treating animal subjects, the compositions of the invention can be formulated as pharmaceutical or veterinary compositions. Depending on the subject to be treated, the mode of administration, and the type of treatment desired, e.g., prevention, prophylaxis, therapy; the compositions are formulated in ways consonant with these parameters. A summary of such techniques is found in Remington's Pharmaceutical Sciences, latest edition, Mack Publishing Co., Easton, Pa.

The preparation of therapeutic compositions containing small organic molecules polypeptides, analogs or active fragments as active ingredients is well understood in the art. The compositions of the present invention may be administered parenterally, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Formulations may be prepared in a manner suitable for systemic administration or for topical or local administration. Systemic formulations include, but are not limited to those designed for injection (e.g., intramuscular, intravenous or subcutaneous injection) or may be prepared for transdermal, transmucosal, nasal, or oral administration. Such compositions may be prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. The formulation will generally include a diluent as well as, in some cases, adjuvants, buffers, preservatives and the like. In addition, if desired, the composition can contain minor amounts of auxiliary substances such as wetting or emulsifying agents, pH buffering agents which enhance the effectiveness of the active ingredient.

A small organic molecule/compound, a polypeptide, an analog or active fragment thereof can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example,سodium, potassium, ammonium, calcium, or ferric hydroxides, and such organic bases as isopropylamine, trimethylamine, 2-ethylamino ethanol, histidine, procaine, and the like. For oral administration, the compositions can be administered also in liposomal compositions or as microemulsions. Suitable forms include syrups, capsules, tablets, as is understood in the art.

The compositions of the present invention may also be administered locally to sites in subjects, both human and other vertebrates, such as domestic animals, rodents and livestock, using a variety of techniques known to those skilled in the art. For example, these may include sprays, lotions, gels or other vehicles such as alcohols, polyglycols, esters, oils and silicones.

The administration of the compositions of the present invention may be pharmacokinetically and pharmacodynamically controlled by calibrating various parameters of administration, including the frequency, dosage, duration mode and route of administration. Variations in the dosage, duration and mode of administration may also be manipulated to produce the activity required.

The therapeutic adenosine receptor modulator (e.g. inhibitor) compositions are conventionally administered in the form of a unit dose, for instance intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the agent selected for treating the subject, the dosage formulation, and in a therapeutically effective amount. If one desires to achieve the desired effect in vitro, the effective amounts may range from about 0:1 nM to about 10 µM, more preferably about 0.1 µM to about 5 µM, and most preferably from about 0.1 nM to about 1 nM. The desired effect refers to the effect of the agent on reducing or inhibiting osteoclast differentiation or stimulation, reducing or inhibiting bone resorption and reducing or inhibiting loosening of a medical prosthesis. Moreover, the quantity of the adenosine receptor agonist to be administered depends on the subject to be treated, and degree of stimulation or mimicry of the adenosine receptor desired or the extent or severity of bone resorption. Precise amounts of active ingredient required to be administered depend on the judgment of the practitioner and are peculiar to each individual. However, suitable dosages to achieve the desired therapeutic effect in vivo may range from about 0.1 mg/kg body weight per day to about 200 mg/kg body weight per day, or from about 1.0 mg/kg body weight per day to about 100 mg/kg body weight per day, preferably about 25 mg/kg body weight per day to about 50 mg/kg body weight per day. In a particular embodiment, the term "about" means within 20%, preferably within 10%, and more preferably within 5%. The preferred dose will depend on the route of administration. However, dosage levels are highly dependent on the nature of the disease or situation, the condition of the subject, the judgment of the practitioner, and the frequency and mode of administration. If the oral route is employed, the absorption of the substance will be a factor effecting bioavailability. A low absorption will have the effect that in the gastro-intestinal tract higher concentrations, and thus higher dosages, will be necessary. Suitable regimes for initial administration and further administration are also variable, but are typified by an initial administration followed by repeated doses at one or more hour intervals by a subsequent injection or other administration. Alternatively, continuous intravenous infusion sufficient to maintain desired concentrations, e.g. in the blood, are contemplated. The composition may be administered as a single dose multiple doses or over an established period of time in an infusion.

It will be understood that the appropriate dosage of the substance should suitably be assessed by performing animal model tests, where the effective dose level (e.g., $ED_{50}$) and the toxic dose level (e.g. $TD_{50}$) as well as the lethal dose level (e.g. $LD_{50}$ or $LD_{10}$) are established in suitable and acceptable animal models. Further, if a substance has proven efficient in such animal tests, controlled clinical trials should be performed.

The compounds or compositions of the present invention may be modified or formulated for administration at the site of pathology. Such modification may include, for instance, formulation which facilitate or prolong the half-life of the compound or composition, particularly in the environment. Additionally, such modification may include the formulation of a compound or composition to include a targeting protein or sequence which facilitates or enhances the uptake of the compound/composition to bone or bone precursor cells. In a particular embodiment, such modification results in the preferential targeting of the compound to bone or bone precursor cells versus other locations or cells. In one embodiment, a tetracycline, tetracycline family or bisphosphonate may be utilized to target the compound or composition of the present invention to bone or bone cells, including osteoclasts and osteoclast precursors. Novel heterocycles as bone targeting compounds are disclosed in U.S. Patent Publication No. 2002/0103161 $A_1$, which is incorporated herein by reference in its entirety.

Pharmaceutically acceptable carriers useful in these pharmaceutical compositions include, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Sterile injectable forms of the compositions may be aqueous or oleaginous suspensions. The suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Parenteral formulations may be a single bolus dose, an infusion or a loading bolus dose followed with a maintenance dose. These compositions may be administered once a day or on an "as needed" basis.

The pharmaceutical compositions may be orally administered in any orally acceptable dosage form including, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically. Topical application can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The invention also provides a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

The invention also provides prosthetic devices having an adenosine receptor modulating agent such as an adenosine $A_{2A}$ receptor agonist thereon or therein. The adenosine receptor modulating agent such as an adenosine $A_{2A}$ receptor agonist may be present in a composition applied to one or more surfaces of the prosthetic device or the adenosine receptor modulating agent such as an adenosine $A_{2A}$ receptor agonist may be present within the prosthetic device. That is, the adenosine receptor modulating agent such as an adenosine $A_{2A}$ receptor agonist, may be present within the very matrix of the prosthetic device such as for instance within the cement, e.g. methylmethacrylate cement that forms the prosthetic device.

Effective Doses

Toxicity and therapeutic efficacy of compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to unaffected cells and, thereby, reduce side effects.

The data obtained from cell culture assays and animal studies can be used in formulating a dose range for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to optimize efficacious doses for administration to humans. Plasma levels can be measured by any technique known in the art, for example, by high performance liquid chromatography.

In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. Normal dose ranges used for particular therapeutic agents employed for specific diseases can be found in the Physicians' Desk Reference 54$^{th}$ Edition (2000).

EXAMPLES

The following examples are set forth to provide those of ordinary skill in the art with a description of how to make and use the methods and compositions of the invention, and are not intended to limit the scope thereof. Efforts have been made to insure accuracy of numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Bone mineral density in 6-month old $A_{2A}$ receptor knock-out mice and otherwise genetically identical wild type mice was determined. The $A_{2A}$ receptor knockout mice had significantly lower bone mineral density, and examination of their long bones showed increased bone resorption and increased numbers of osteoclasts. Electron microscopy demonstrated that the osteoclasts appeared to be much more active in bone resorption than in the wild type mice. When studied in vitro RAW264.7 cells, a murine cell line, can be induced to differentiate into osteoclast-like cells. Culture of these cells in the presence of an adenosine $A_{2A}$ receptor antagonist inhibited osteoclast formation. Bone mineral density was determined in anesthetized mice by use of quantitative Xray densitometry (DEXA scan, Piximus GE).

Electron Microscopy of Osteoclasts

Both tibiae and femora of five animals will be fixed in 2.5% glutaraldehyde in 0.1 M sodium cacodylate buffer (pH 7.4) for 12 hours at ambient temperature. After being rinsed three times for 20 min in the same buffer, the material will be postfixed for 6 hours in 1% osmium tetroxide (in 0.1 M sodium cacodylate buffer), dehydrated in acetone and embedded. Sections are prepared, stained with Cathepsin K and examined in the electron microscope. The thin sections are scanned systematically and all osteoclasts encountered are photographed.

Characterization of Osteoclasts

Osteoclast formation was evaluated by quantification of TRAP-positive MNCs as described previously. TRAP is preferentially expressed at high levels in osteoclasts and is considered, especially in the mouse, to be an osteoclast marker. After incubation, cells on wells were washed in PBS, fixed in 4% paraformaldehyde for 10 min, and stained for acid phosphatase in the presence of 0.3 M sodium tartrate (Sigma-Aldrich). The substrate used was napthol AS-BI phosphate (Sigma-Aldrich). Only those cells that were strongly TRAP-positive (dark red) and have more than 3 nuclei were counted by light microscopy. To evaluate the size of the Osteoclast over time, we counted the number of nuclei per OCL in 50 OCLs for each of the three wells (n=150). The mean number of nuclei per OCL (MNN) and SE were calculated for each time-point, and ANOVA analysis was performed to determine statistically significant differences.

Example 2

A model of prosthesis loosening and bone resorption will be established. A subcutaneous air pouch will be created on the dorsum of a mouse. Ultra high molecular weight polyethylene debris will be implanted into the air pouch followed by implantation of calvaria from syngeneic mice. The material will be harvested from the mice after 14 days, and bone resorption and inflammation will be assessed. An adenosine $A_{2A}$ receptor agonist (CGS21680) will be mixed into methylmethacrylate glue applied to the calvarial bone in some animals or methylmethacrylate glue alone applied to the calvarial bone in controls. Numbers of TRAP+ osteoclasts, bone resorption (microCT), bone collagen content (von Gieson stain), inflammatory cytokine production (IL-1, TNF, IL-6) in exudates (ELISA) and by FISH in bone will be assessed according to the procedures described by Ren, et al., 2006, *Journal of Orthopaedic Research* 24:1575-1586.

Similar preparations in adenosine $A_{2A}$ receptor knockout mice will also be studied to confirm the specificity of the effect. The data will demonstrate that adenosine $A_{2A}$ receptor agonists can be used to prevent bone resorption in a simple model of prosthesis loosening. The data will further confirm that $A_{2A}$ receptor agonists may be used for preventing periprosthetic bone resorption. Currently two adenosine $A_{2A}$ receptor agonists are in testing for topical application for wound healing (King, currently in Phase II trials) and as a coronary vasodilator for pharmacologic stress testing (ATL, Inc. and Bristol-Myers-Squibb, Phase I recently reported). Both agents are extremely short-lived and relatively non-toxic.

Example 3

Background. Osteoclasts are bone-resorbing, multinucleated giant cells that are essential for bone remodeling and that are formed through the fusion of mononuclear precursor cells. Osteoclasts differentiate from hemopoietic precursors of the monocyte/macrophage lineage in the presence of M-CSF and receptor activator of NF-kB ligand (RANKL). Deficiency of osteoclasts leads to osteopetrosis, a condition characterized by increased bone density. Nonetheless, most bone diseases are due to increased bone resorption by osteoclasts and inhibition of osteoclast-mediated bone resorption is a primary therapeutic objective. Indeed, most current therapies for osteoporosis are directed at inhibition of osteoclast function. Adenosine, a potent endogenous physiological mediator, regulates a wide variety of physiological processes via interaction with one or more of four G protein-coupled receptors ($A_1$, $A_{2A}$, $A_{2B}$ and $A_3$), expressed on many cell types. Because we have previously reported that adenosine $A_{2A}$ receptor occupancy is required for fusion of stimulated human monocytes to form giant cells in vitro we determined whether there was a similar requirement for $A_{2A}$ receptor occupancy in osteoclast formation and function in vitro and in vivo models.

Materials and Methods

RAW264.7 is a macrophage cell line having the capacity to form osteoclast-like cells. Because the RAW264.7 cells provide an excellent in vitro model for dissecting the cellular and molecular regulation of osteoclast differentiation and activation, we studied the effect of adenosine $A_{2A}$ receptors on the osteoclasts generated from the RAW264.7 cells.

Total RNA extraction/RT-PCR from RAW264.7, splenocyte and bone marrow cells. After the cultured cells became confluent in tissue culture flasks and were passaged three times, the cell suspensions were lysed in Trizol reagent (Invitrogen Life Technologies, UK), and total RNA from dissolved specimens was extracted according to the manufacturer's instructions. First, single stranded complementary DNA (cDNA) was synthesized from total RNA from each sample using a cDNA synthesis kit (Invitrogen Life Technologies, UK). cDNA was then amplified by polymerase chain reaction (PCR) to generate products corresponding to mRNA encoding mice gene products for adenosine receptors $A_1$, $A_{2A}$, $A_{2B}$ and $A_3$ and GAPDH mRNAs were assessed by RT-PCR.

Cell Culture and Osteoclastogenesis. Raw264.7 cells were cultured in 24 well plates ($5\times10^4$/ml) with α-MEM and 10% heat inactivated Fetal Bovine Serum (FBS). Cells were then incubated with 30 ng/ml of recombinant mouse RANKL in the presence of either $A_{2A}$ agonist (CGS 21680) or antagonist (ZM241385). After four days of culture, cells were fixed with 10% formalin and stained for tartrate-resistant acid phosphatase (TRAP). Osteoclasts were identified as TRAP-positive cells with 3 or more nuclei. The number of TRAP-positive multinucleated cells/well was then enumerated.

Western blotting. Osteoclast precursors were preincubated with or without CGS21680 (1 μg/ml) or ZM241385 (1 μg/ml) for 4 days and then stimulated with RANKL (30 ng/ml) for the indicated period. For isolation of total proteins, cells were washed twice with PBS and lysed in RIPA buffer. Proteins were estimated and boiled with sample buffer for 5 min and were subjected to electrophoresis on 10% SDS-PAGE. Proteins were transferred onto a nitrocellulose membrane. Membranes were blocked for 2 hours in blocking solution (5% nonfat dry milk in TBS containing 0.1% Tween 20) and exposed to primary Abs overnight at 4° C. After washing, the membranes were incubated for 1 hour at room temperature with secondary Ab, and the proteins were detected using ECL reagents according to the manufacturer's instructions. To reprobe the membranes with other Abs, the membranes were stripped with 100 mM 2-ME, 2% SDS, and 62.5 mM Tris-HCl (pH 6.9) for 20 min at 50° C., followed by immunoblotting as described above.

Bone density measurements. In vivo bone density measurements in $A_{2A}$ WT (wild type) and $A_{2A}$ KO (knock out) mice were performed by dual energy x-ray absorptiometry, using a PIXImus densitometer (Lunar Corp., Madison, Wis.). Measurements were made at 6 months of age. Anesthetized mice (30 mg ketamine/kg body wt and 3 mg xylazine/kg body wt, ip) were placed in the prone position, and scans were performed and an acquisition time of 5 min.

Micro-X-Ray Computed Tomography (ACT) analysis of bone mass. For measurements of the bone volume (trabecular bone volume (BV/TV)), the femurs from four $A_{2A}$ WT and 4 $A_{2A}$KO mice were subjected to μCT analysis with MS-8 (MS-8, GE Healthcare, London, Ontario, Canada) at 18 μm isotropic resolution-scans calibrated by air, water and a mineral standard material phantom/Parker algorithm for digital reconstruction. The fractional bone volume (BV/TV) was measured in a cortical-rectangle area in the proximal diaphysis (1.8 mm) parts.

Electron microscopy of osteoclasts. Femurs of five animals will be fixed in 2.5% glutaraldehyde in 0.1 M sodium cacodylate buffer (pH 7.4) for 12 hours at ambient temperature. After being rinsed three times for 20 min in the same buffer, the material will be postfixed for 6 hours in 1% osmium tetroxide (in 0.1 M sodium cacodylate buffer), dehydrated in acetone and embedded. Sections will be prepared, stained with Cathepsin K and examined in an electron microscope.

Results

Osteoclasts express mRNA and protein for all four adenosine receptors. It was determined whether osteoclasts derived from bone marrow osteoclast precursors, splenocyte osteoclast precursors or the murine cell line RAW264.7 which differentiates into osteoclast like cells, express adenosine receptors. We initially measured mRNA levels for specific adenosine receptors in each of the cells and cell lines. As shown in FIG. 1A, all of these cells and cell lines express message for all four adenosine receptors. As shown in FIG. 1B, Western Blot analysis of bone marrow-derived osteoclast lysates demonstrates the presence of all four adenosine receptors.

Figure 2:
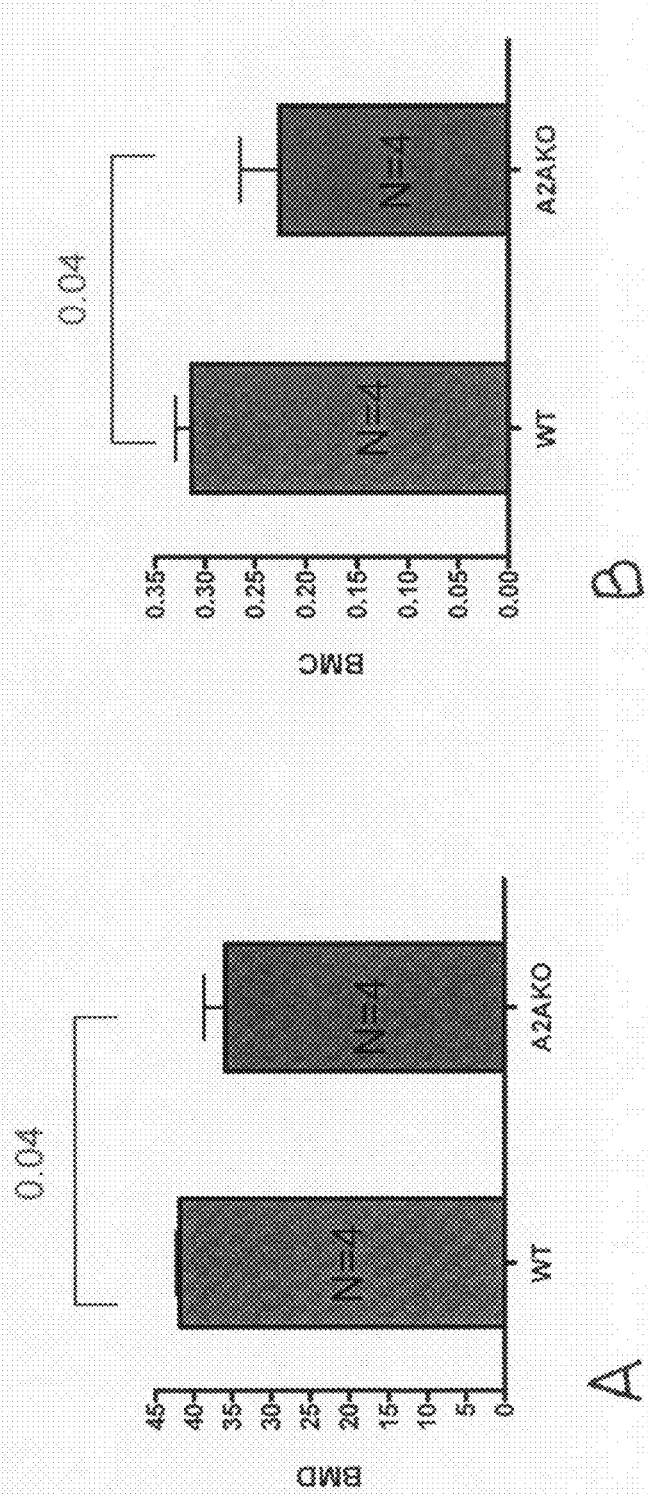
FIG. 2 demonstrates that both bone mineral density (FIG. 2A) and bone mineral $Ca^{++}$ (FIG. 2B) are diminished in adenosine $A_{2A}$ receptor knockout mice suggesting that adenosine receptor knockout mice either have increased bone absorption or diminished bone production.

Adenosine $A_{2A}$ receptor knockout mice have diminished bone density and bone mineral $Ca^{++}$. As shown in FIG. 2, both bone mineral density and bone mineral $Ca^{++}$ are diminished in adenosine $A_{2A}$ receptor knockout mice. These findings suggest that adenosine receptor knockout mice either have increased bone absorption or diminished bone production.

Figure 3:
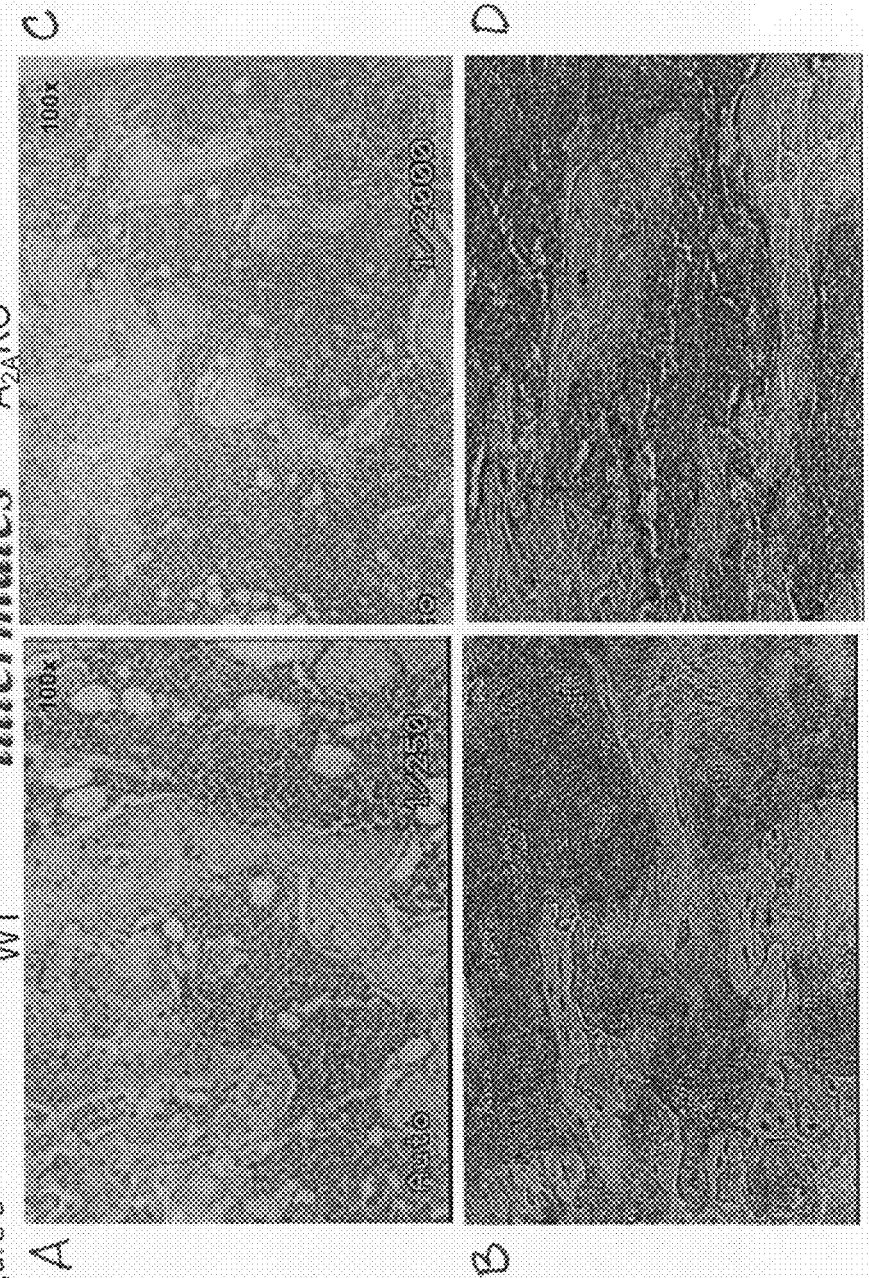
FIG. 3 demonstrates that adenosine $A_{2A}$ receptor knockout mice have evidence for increased bone resorption and increased numbers of osteoclasts in their bones. Alcian Blue staining of decalcified bone from WT (FIGS. 3A, B) and $A_{2A}$ knockout (FIGS. 3 C, D) mice demonstrates a marked increase in the number of osteoclasts and diminished bone substance in the $A_{2A}$ receptor knockout mice.

Adenosine $A_{2A}$ receptor knockout mice have evidence for increased bone resorption and increased numbers of osteoclasts in their bones. Alcian Blue staining of decalcified bone from WT (wild type) and adenosine $A_{2A}$ knockout mice demonstrates a marked increase in the number of osteoclasts and diminished bone substance in the adenosine $A_{2A}$ receptor knockout mice (FIG. 3).

Figure 4:
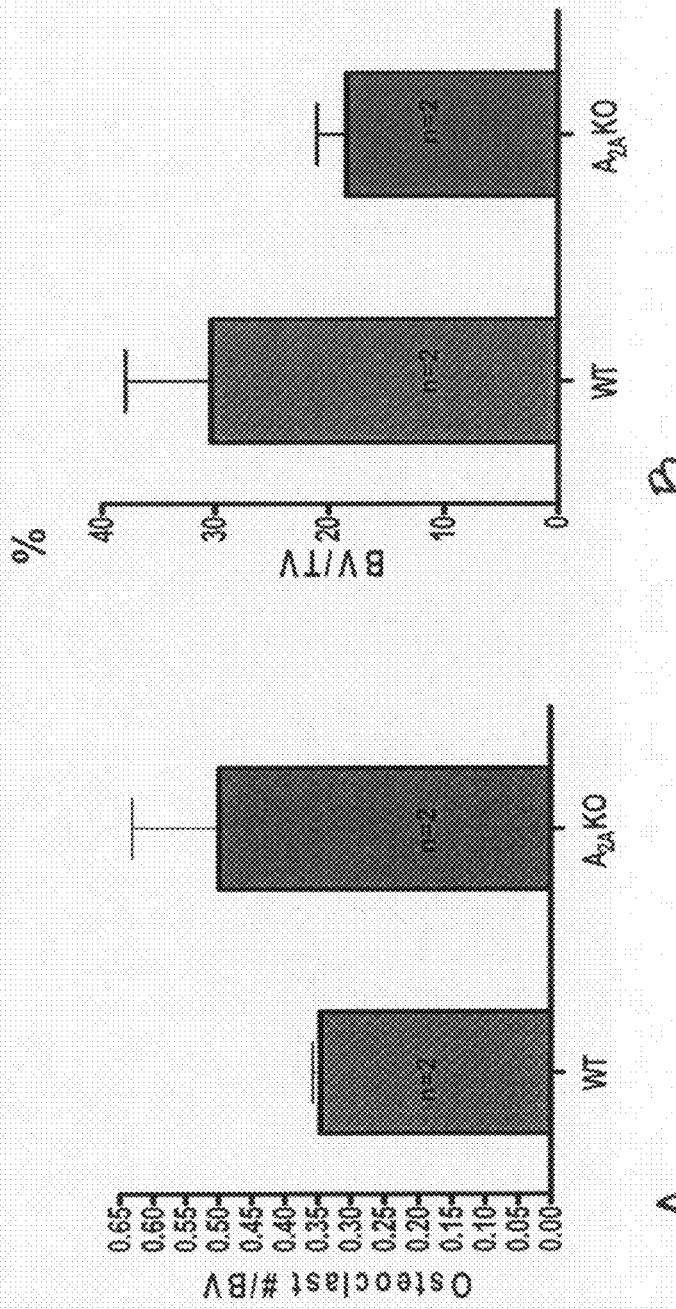
FIG. 4 demonstrates the increased number of osteoclasts correlates with diminished bone mineral density. The increased number of osteoclasts present in the bones of $A_{2A}$ KO mice, as compared to WT mice (FIG. 4A) correlates with the diminished bone mineral density observed by DEXA scan of these mice (FIG. 4B).

The increased number of osteoclasts correlates with diminished bone mineral density. The increased number of osteoclasts present in the bones of $A_{2A}$ KO mice, as compared to WT mice, correlates with the diminished bone mineral density observed by DEXA scan of these mic (FIG. 4).

Figure 5:
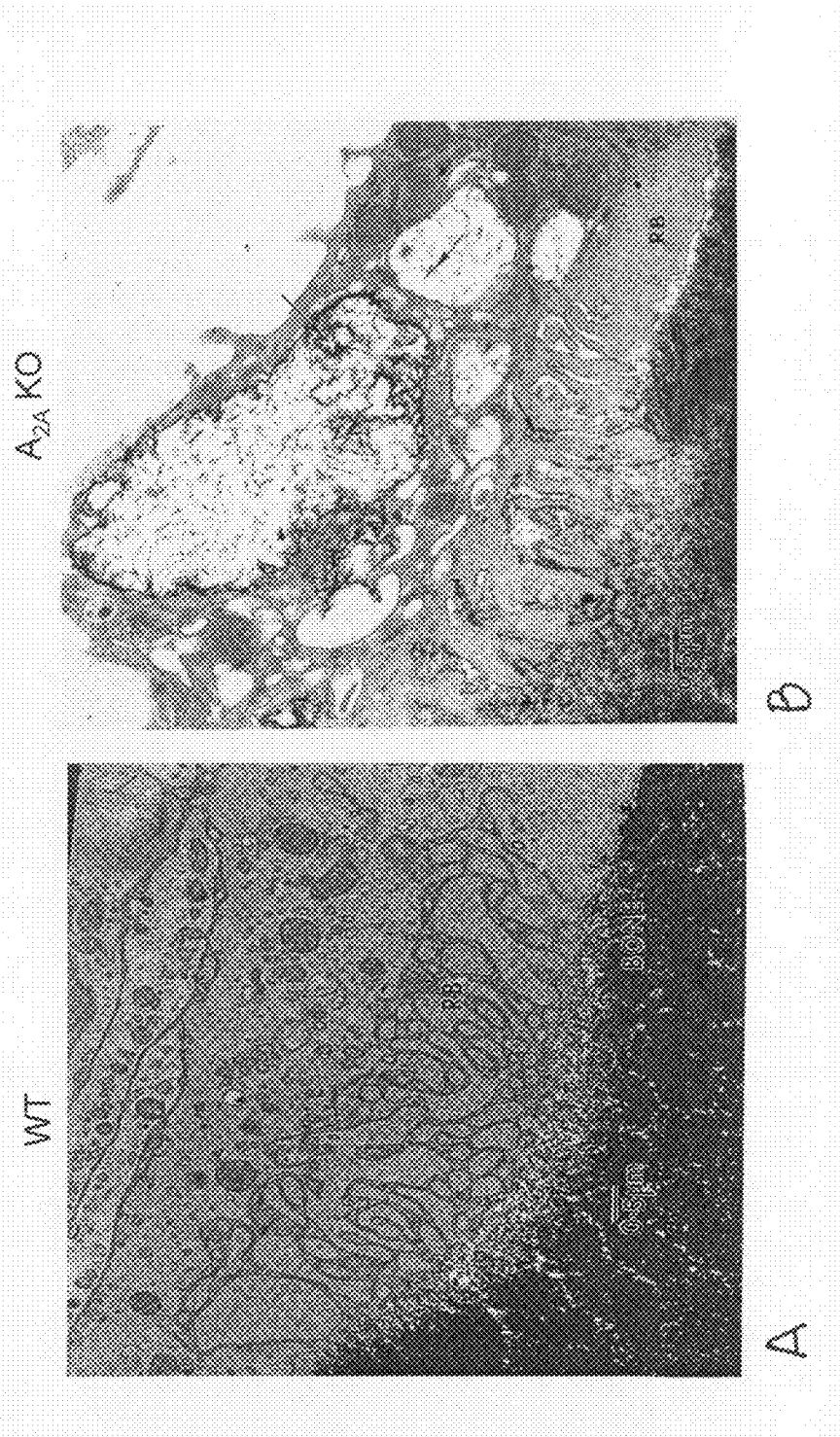
FIG. 5 provides electron microscopy demonstrating greater apparent activity of osteoclasts in $A_{2A}$ KO mice. Examination of bone by electron microscopy demonstrates larger bone resorption pits (clear areas) in the bones of $A_{2A}$ receptor knockout mice (FIG. 5B) than wild type mice (FIG. 5A).

Electron Microscopy demonstrates greater apparent activity of osteoclasts in $A_{2A}$ KO mice. Examination of bone by electron microscopy demonstrates larger bone resorption pits (clear areas) in the bones of $A_{2A}$ receptor knockout mice than wild type mice (FIG. 5).

MicroCT of bones from $A_{2A}$ knockout mice demonstrates diminished cortical and trabecular bone in the KO mice as compared to WT mice. By all measures of bone substance, there is a reduction in both cortical and trabecular bone in the femurs of $A_{2A}$ receptor knockout ($A_2$KO) mice as compared to their wild type littermates (WT) (Table 1).

TABLE 1

Quantitative Micro CT Analysis of the Proximal Femurs of 4-Month-Old WT and $A_{2A}$ KO Mice

|  | WT | $A_2$KO | t-test |
|---|---|---|---|
| Bone Volume/Tissue Volume BV/TV | 22.61 ± 2.154 N = 3 | 17.49 ± 0.98 N = 3 | 0.04 |
| Trabecular number (Tb. N.) | 5.8 ± 0.07 N = 3 | 4.4 ± 0.15 N = 3 | 0.0006 |
| Trabecular separation (Tb. Sep.) | 0.13 ± 0.004 N = 3 | 0.19 ± 0.006 N = 3 | 0.001 |
| Cortical area | 0.68 ± 0.04 N = 3 | 0.6 ± 0.016 N = 3 | 0.05 |
| Total area | 1.5 ± 0.03 N = 3 | 1.3 ± 0.02 N = 3 | 0.02 |
| BMC | 0.01 ± 0.0008 N = 3 | 0.01 ± 0.0003 N = 3 | 0.06 |
| Outer Perimeter | 4.6 ± 0.04 N = 3 | 4.4 ± 0.04 N = 3 | 0.006 |
| TMC | 1.9 ± 0.12 N = 3 | 1.7 ± 0.05 N = 3 | 0.05 |

Figure 6:
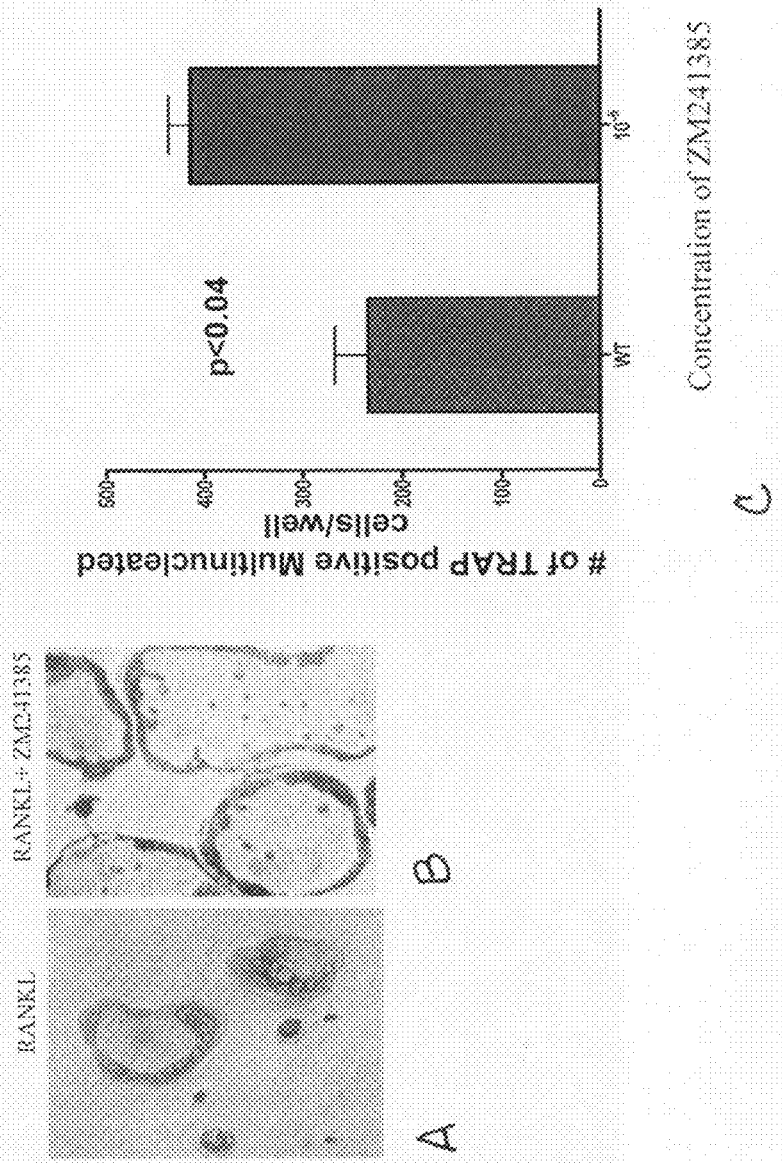
FIG. 6 demonstrates that adenosine $A_{2A}$ receptor blockade diminishes osteoclast formation in vitro by RAW264.7 cells induced to undergo osteoclast differentiation. Adenosine $A_{2A}$ receptor antagonist treated RAW264.7 cells (FIG. 6B) form an increased number of multinucleated TRAP+ osteoclasts in culture than untreated RAW264.7 cells (FIG. 6A). This is graphically demonstrated in FIG. 6C.

Adenosine $A_{2A}$ receptor blockade diminishes osteoclast formation in vitro by RAW264.7 cells induced to undergo osteoclast differentiation. To better understand why adenosine $A_{2A}$ receptor knockout mice have diminished bone density as compared to wild type mice, the effect of an adenosine $A_{2A}$ receptor antagonist on osteoclast formation was determined. As shown in FIG. 6 adenosine $A_{2A}$ receptor antagonist treated RAW264.7 cells form an increased number of multinucleated TRAP+ osteoclasts in culture than untreated RAW264.7 cells.

Figure 7:
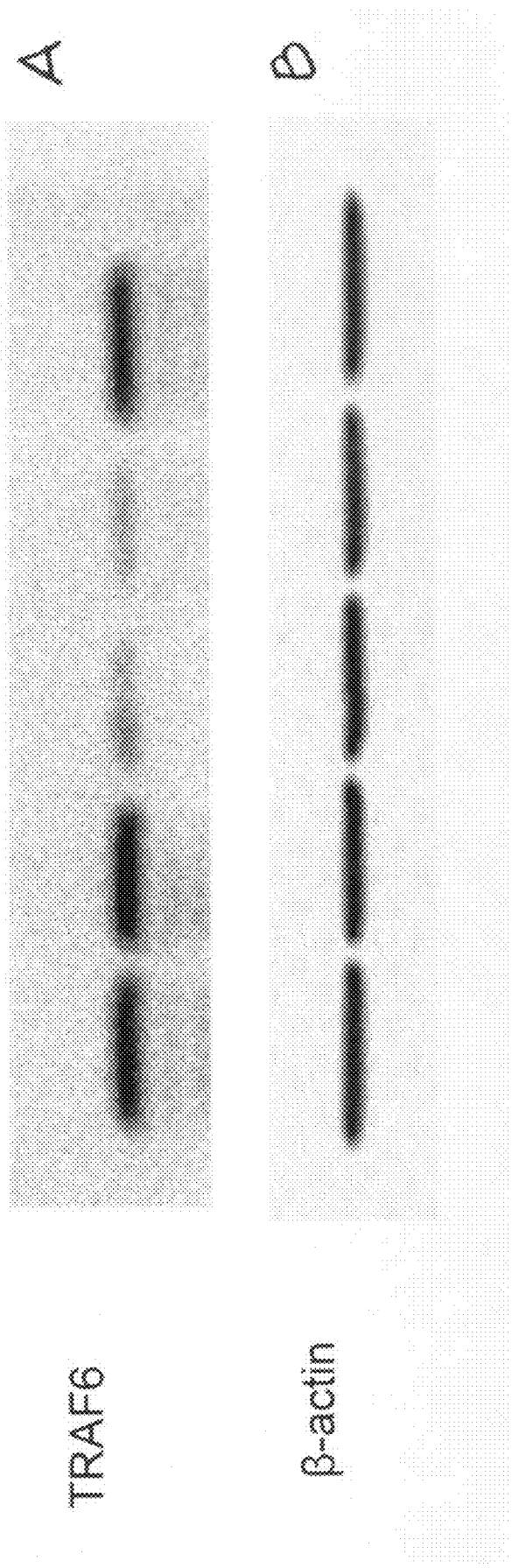
FIG. 7 demonstrates that adenosine $A_{2A}$ receptor blockade downregulates TRAF6 protein in RAW264.7 cells (FIG. 7A) as compared to β-actin (FIG. 7B). $A_1$ adenosine receptor blockade diminishes TRAF6 protein, a critical signaling protein for osteoclast differentiation, in bone marrow osteoclasts and RAW264.7 cells. To determine whether adenosine $A_{2A}$ receptors regulate osteoclast differentiation by a similar mechanism, TRAF6 levels in RAW264.7 cells treated with an adenosine $A_1$ receptor antagonist, an $A_{2A}$ agonist and antagonist were determined. Both the $A_1$ receptor antagonist and $A_{2A}$ receptor agonist diminish TRAF6 levels in RAW264.7 cells.

Adenosine $A_{2A}$ receptor blockade downregulates TRAF6 protein in RAW264.7 cells. It was previously demonstrated that $A_1$ adenosine receptor blockade diminishes TRAF6 protein, a critical signaling protein for osteoclast differentiation, in bone marrow osteoclasts and RAW264.7 cells. To determine whether adenosine $A_{2A}$ receptors regulate osteoclast differentiation by a similar mechanism, TRAF6 levels in RAW264.7 cells treated with an adenosine $A_1$ receptor antagonist, an $A_{2A}$ agonist and antagonist were determined. As shown in FIG. 7, both the $A_1$ receptor antagonist and $A_{2A}$ receptor agonist diminish TRAF6 levels in RAW264.7 cells.

Summary. All adenosine receptor subtypes ($A_1$, $A_{2A}$, $A_{2B}$, $A_3$) are expressed in RAW264.7 cells and RAW264.7 derived osteoclasts. Blockade of adenosine $A_{2A}$ receptors enhances osteoclast formation in cultured RAW264.7 cells. Blockade of adenosine $A_{2A}$ receptors enhances osteoclast formation and function in the mouse model. Adenosine $A_{2A}$ receptor knockout mice have osteoporosis. These results demonstrate that adenosine $A_{2A}$ receptors regulate bone homeostasis and serve as targets for drugs that prevent bone loss.

The invention claimed is:

1. A method for inhibiting bone resorption comprising administering to a subject a therapeutically effective amount of an adenosine receptor agonist-via an implanted device.

2. The method of claim 1 wherein the adenosine receptor is selected from the group consisting of $A_1$, $A_{2A}$, $A_{2B}$ and $A_3$.

3. The method of claim 2 wherein the adenosine receptor is an $A_{2A}$ receptor.

4. The method of claim 1 wherein and the agonist is an adenosine receptor $A_{2A}$ agonist.

5. The method of claim 4 wherein and the adenosine receptor $A_{2A}$ agonist is a selective adenosine receptor agonist.

6. The method of claim 4 wherein the adenosine $A_{2A}$ receptor agonist is selected from the group consisting of CGS 21680, IB-MECA and R-PIA.

7. The method of claim 4 wherein the adenosine $A_{2A}$ receptor agonist is administered in combination with one or more of other compounds or agents for inhibiting bone resorption, osteoclast differentiation and stimulation and prosthesis loosening or for reducing inflammation.

8. A method for inhibiting differentiation and stimulation of osteoclasts comprising administering to a subject a therapeutically effective amount of an adenosine receptor agonist via an implanted device.

9. The method of claim 8 wherein the adenosine receptor is selected from the group consisting of $A_1$, $A_{2A}$, $A_{2B}$ and $A_3$.

10. The method of claim 9 wherein the adenosine receptor is an $A_{2A}$ receptor.

11. The method of claim 8 wherein and the agonist is an adenosine receptor $A_{2A}$ agonist.

12. The method of claim 11 wherein and the adenosine receptor $A_{2A}$ agonist is a selective adenosine receptor agonist.

13. The method of claim 11 wherein the adenosine $A_{2A}$ receptor agonist is selected from the group consisting of CGS 21680, IB-MECA and R-PIA.

14. The method of claim 11 wherein the adenosine $A_{2A}$ receptor agonist is administered in combination with one or more of other compounds or agents for inhibiting bone resorption, osteoclast differentiation and stimulation and prosthesis loosening or for reducing inflammation.

15. A method of inhibiting or reducing loosening of a medical prosthesis comprising administering to the subject an amount of an adenosine receptor agonist effective to inhibit or reduce bone resorption via an implanted device.

16. The method of claim 15 wherein the adenosine receptor is selected from the group consisting of $A_1$, $A_{2A}$, $A_{2B}$ and $A_3$.

17. The method of claim 16 wherein the adenosine receptor is an $A_{2A}$ receptor.

18. The method of claim 15 wherein and the agonist is an adenosine receptor $A_{2A}$ agonist.

19. The method of claim 18 wherein and the adenosine receptor $A_{2A}$ agonist is a selective adenosine receptor agonist.

20. The method of claim 18 wherein the adenosine $A_{2A}$ receptor agonist is selected from the group consisting of CGS 21680, IB-MECA and R-PIA.

21. The method of claim 18 wherein the adenosine $A_{2A}$ receptor agonist is administered in combination with one or more of other compounds or agents for inhibiting bone resorption, osteoclast differentiation and stimulation and prosthesis loosening or for reducing inflammation.

22. A prosthetic device comprising an adenosine receptor agonist in an amount sufficient to inhibit osteoclast differentiation and stimulation, bone resorption, or loosening of a prosthetic device.

23. The prosthetic device of claim 22 wherein the adenosine receptor agonist is an adenosine $A_{2A}$ receptor agonist.

24. The prosthetic device of claim 22 wherein the adenosine receptor agonist is present within the prosthetic device.

25. The method of claim 20 wherein the adenosine $A_{2A}$ receptor agonist is CGS 21680.

* * * * *